United States Patent
Brown et al.

(10) Patent No.: US 7,034,032 B2
(45) Date of Patent: Apr. 25, 2006

(54) CYCLOPENTAN-2-OL-1-YL-[1,2,3]TRIAZOLO[4,5-D]PYRIMIDINE COMPOUNDS

(75) Inventors: Roger Brown, Leicestershire (GB); Simon Guile, Leicestershire (GB); Garry Pairaudeau, Leicestershire (GB); Brian Springthorpe, Leicestershire (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/415,248

(22) PCT Filed: Nov. 7, 2001

(86) PCT No.: PCT/SE01/02471

§ 371 (c)(1), (2), (4) Date: Apr. 24, 2003

(87) PCT Pub. No.: WO02/38570

PCT Pub. Date: May 16, 2002

(65) Prior Publication Data

US 2004/0023988 A1    Feb. 5, 2004

(30) Foreign Application Priority Data

Nov. 9, 2000   (SE) .................... 0004099

(51) Int. Cl.
- C07D 4487/04 (2006.01)
- A61K 31/437 (2006.01)
- A61P 9/08 (2006.01)

(52) U.S. Cl. ................ 514/261.1; 544/254

(58) Field of Classification Search ........... 514/261.1; 544/254
See application file for complete search history.

(56) References Cited

FOREIGN PATENT DOCUMENTS

| EP | 0 368 640 A2 | 5/1990 |
|---|---|---|
| WO | WO 99/05143 A1 | 2/1999 |

OTHER PUBLICATIONS

West, Anthony R., Solid State Chemistry and its Applications, Wiley, New York, 1988, pp. 358 & 365.*
Storey, R.F. et al, Thromb. Haemost., 2001, 85(3), pp. 401-407, Medline Abstract PMID 11307804.*

* cited by examiner

*Primary Examiner*—Thomas C. McKenzie
(74) *Attorney, Agent, or Firm*—Fish & Neave IP Group Ropes & Gray LLP

(57) ABSTRACT

The invention provides novel 1,2,3-triazolo[4,5-d]pyrimidine compounds, such as those represented by formula (I):

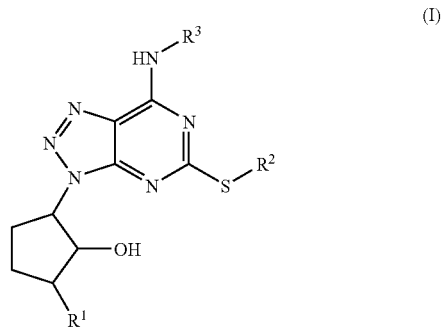

their use as medicaments, particularly in platelet aggregation disorders, compositions containing them and processes for their preparation.

16 Claims, No Drawings

CYCLOPENTAN-2-OL-1-YL-[1,2,3]TRIAZOLO[4,5-D]PYRIMIDINE COMPOUNDS

CROSS-REFERENCE TO RELATED APPLICATIONS

This application is a national stage filing under 35 U.S.C. 371 of International Application No. PCT/SE01/02471, filed Nov. 7, 2001, which claims priority from Sweden Patent Application No. 0004099-8, filed Nov. 9, 2000, the specifications of each of which are incorporated by reference herein. International Application No. PCT/SE01/02471 was published under PCT Article 21 (2) in English.

FIELD OF THE INVENTION

The present invention provides novel 1,2,3-triazolo[4,5-d]pyrimidine analogues, their use as medicaments, compositions containing them and processes for their preparation.

BACKGROUND OF THE INVENTION

Platelet adhesion and aggregation are initiating events in arterial thrombosis. Although the process of platelet adhesion to the sub-endothelial surface may have an important role to play in the repair of damaged vessel walls, the platelet aggregation that this initiates can precipitate acute thrombotic occlusion of vital vascular beds, leading to events with high morbidity such as myocardial infarction and unstable angina. The success of interventions used to prevent or alleviate these conditions, such as thrombolysis and platelet-mediated occlusion or re-occlusion also compromises angioplasty.

A number of converging pathways lead to platelet aggregation. Whatever the initial stimulus, the final common event is a cross-linking of platelets by binding of fibrinogen to a membrane-binding site, glycoprotein IIb/IIIa (GPIIb/IIIa). The high anti-platelet efficacy of antibodies or antagonists for GPIIb/IIIa is explained by their interference with this final common event. However, this efficacy may also explain the bleeding problems that have been observed with this class of agent. Thrombin can produce platelet aggregation largely independently of other pathways but substantial quantities of thrombin are unlikely to be present without prior activation of platelets by other mechanisms. Thrombin inhibitors such as hirudin are highly effective anti-thrombotic agents, but again may produce excessive bleeding because they function as both anti-platelet and anti-coagulant agents. (The TIMI 9a Investigators (1994), *Circulation* 90, pp. 1624–1630; The Global Use of Strategies to Open Occluded Coronary Arteries (GUSTO) IIa Investigators (1994) *Circulation* 90, pp. 1631–1637; Neuhaus K. L. et. al. (1994) *Circulation* 90, pp. 1638–1642.)

It has been found that ADP acts as a key mediator of thrombosis. A pivotal role for ADP is supported by the fact that other agents, such as adrenaline and 5-hydroxytryptamine (5HT, serotonin) will only produce aggregation in the presence of ADP. The limited anti-thrombotic efficacy of aspirin may reflect the fact that it blocks only one source of ADP which is that released in a thromboxane-dependent manner following platelet adhesion (see e.g. Antiplatelet Trialists' Collaboration (1994), *Br. Med. J.* 308, pp. 81–106 and Antiplatelet Trialists' Collaboration (1994), *Br. Med. J.* 308, pp. 159–168). Aspirin has no effect on aggregation produced by other sources of ADP, such as damaged cells or ADP released under conditions of turbulent blood flow.

ADP-induced platelet aggregation is mediated by the $P_{2T}$ receptor subtype located on the platelet membrane. The $P_{2T}$ receptor (also known as $P2Y_{ADP}$ or $P2T_{AC}$) is primarily involved in mediating platelet aggregation/activation and is a G-protein coupled receptor, which is as yet uncloned. The pharmacological characteristics of this receptor have been described, for example, in the references by Humphries et al., *Br. J. Pharmacology*, (1994), 113, 1057–1063, and Fagura et al., *Br. J. Pharmacology* (1998) 124, 157–164. Recently it has been shown that antagonists at this receptor offer significant improvements over other anti-thrombotic agents (see *J. Med. Chem.* (1999) 42, 213). Accordingly there is a need to find further $P_{2T}$ ($P2Y_{ADP}$ or $P2T_{AC}$) antagonists as anti-thrombotic agents.

DESCRIPTION OF THE INVENTION

In a first aspect the invention therefore provides a compound of formula (I):

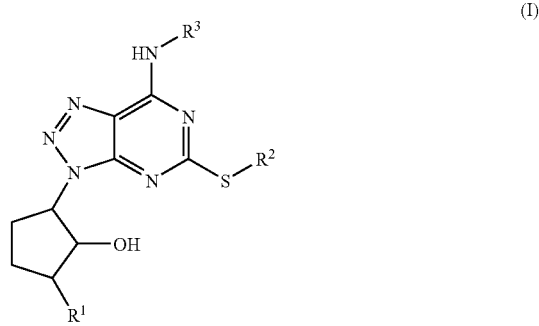

(I)

wherein:

$R^1$ is hydrogen or hydroxy;

$R_2$ is $C_{1-6}$ alkyl, or $C_{1-6}$ haloalkyl, or phenyl optionally substituted by halogen or by $C_{1-6}$ alkyl, optionally substituted by halogen;

$R^3$ is $C_{3-6}$ cycloalkyl, optionally substituted by $R^4$;

$R^4$ is hydrogen or phenyl, optionally substituted by alkyl $C_{1-6}$, halogen, or $C_{1-6}$ alkoxy.

Preferably the compound of formula (I) has the following stereochemistry:

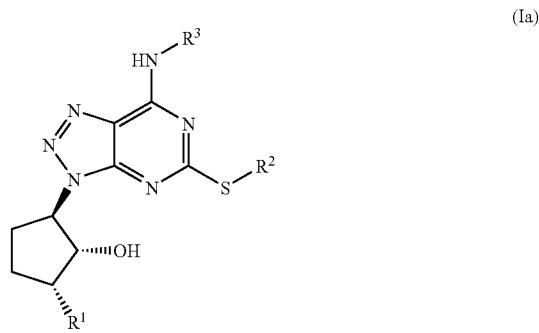

(Ia)

where $R^1$, $R^2$ and $R^3$ and are as defined above.

When R³ is

where R⁴ is defined above, the stereochemistry is preferably

Suitably, R¹ is hydrogen or hydroxy;
Suitably, R² is $C_{1-4}$ alkyl, or $C_{1-4}$ haloalkyl, or phenyl optionally substituted by halogen or by $C_{1-4}$ alkyl, optionally substituted by halogen;
Suitably, R³ is cyclopropyl, optionally substituted by R⁴;
Suitably, R⁴ is hydrogen or phenyl, optionally substituted by halogen or $C_{1-4}$ alkoxy.

Particularly preferred compounds of the invention include:
[1R-[1α,2α,3β(1R*,2S*)]]-3-[7-[(2-Phenylcyclopropyl)amino]-5-(propylthio)-3H-[1,2,3]triazolo[4,5-d]pyrimidin-3-yl]cyclopentane-1,2-diol;
[1R-[1α,2α,3β(1R*,2S*)]]-3-[7-[[2-(4-Methylphenyl)cyclopropyl]amino]-5-(propylthio)-3H-[1,2,3]triazolo[4,5-d]pyrimidin-3-yl]cyclopentane-1,2-diol;
[1R-[1α,2α,3β(1R*,2S*)]]-3-[7-[(2-Phenylcyclopropyl)amino]-5-(methylthio)-3H-[1,2,3]triazolo[4,5-d]pyrimidin-3-yl]cyclopentane-1,2-diol;
[1R-[1α,2α,3β(1R*,2S*)]]-3-[7-[(2-Phenylcyclopropyl)amino]-5-(ethylthio)-3H-[1,2,3]triazolo[4,5-d]pyrimidin-3-yl]cyclopentane-1,2-diol;
[1R-(1α,2α,3β)]-3-[7-(Cyclopropylamino)-5-(propylthio)-3H-[1,2,3]triazolo[4,5-d]pyrimidin-3-yl]cyclopentane-1,2-diol;
[1R-(1α,2α,3β)]-3-[7-(Cyclopropylamino)-5-(3,4-dichlorophenylthio)-3H-[1,2,3]triazolo[4,5-d]pyrimidin-3-yl]cyclopentane-1,2-diol;
[1R-[1α,2α,3β)]]-3-[7-(Cyclopropylamino)-5-(4-trifluoromethylphenylthio)-3H-[1,2,3]triazolo[4,5-d]pyrimidin-3-yl]cyclopentane-1,2-diol;
[1R-[1α,2α,3β(1R*,2S*)]]-3-[7-[(2-Phenylcyclopropyl)amino]-5-(butylthio)-3H-1,2,3-triazolo[4,5-d]pyrimidin-3-yl]cyclopentane-1,2-diol;
[1R-[1α,2α,3β(1R*,2S*)]]-3-[7-[(2-Phenylcyclopropyl)amino]-5-(3,3,3,-trifluoropropylthio)-3H-1,2,3-triazolo[4,5-d]pyrimidin-3-yl]cyclopentane-1,2-diol;
[1R-[1α,2α,3β(1R*,2S*)]]-3-[7-[[2-(4-Chlorophenyl)cyclopropyl]amino]-5-(butylthio)-3H-1,2,3-triazolo[4,5-d]pyrimidin-3-yl]cyclopentane-1,2-diol;
[1R-[1α,2α,3β(1R*,2S*)]]-3-[7-[[2-(4-Fluorophenyl)cyclopropyl]amino]-5-(butylthio)-3H-1,2,3-triazolo[4,5-d]pyrimidin-3-yl]cyclopentane-1,2-diol;
[(1R-[1α,2β(1R*,2S*)]]-2-[7-[(2-Phenylcyclopropyl)amino]-5-(propylthio)-3H-[1,2,3]triazolo[4,5-d]pyrimidin-3-yl]cyclopentanol;
[1R-[1α,2β(1R*,2S*)]]-2-[[7-[2-(4-Methoxyphenyl)cyclopropyl]amino]-5-(propylthio)-3H-[1,2,3]triazolo[4,5-d]pyrimidin-3-yl]cyclopentanol;
[1R-[1α,2β(1R*,2S*)]]-2-[7-[[2-(3,4-Difluorophenyl)cyclopropyl]amino]-5-(propylthio)-3H-[1,2,3]triazolo[4,5-d]pyrimidin-3-yl]cyclopentanol;

or a pharmaceutically acceptable salt or solvate thereof, or a solvate of such a salt.

Compounds of formula (I) can be prepared by:
a) The dihydroxylation of a compound of formula (II),

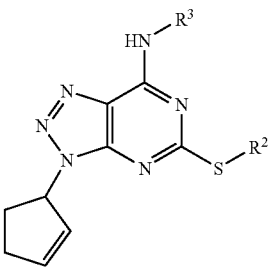

(II)

where R² and R³ are as defined above, preferably using osmium tetroxide, in the presence of an oxidising agent, preferably N-methylmorpholine-N-oxide, under aqueous conditions, preferably in aqueous tetrahydrofuran, preferably at a temperature between 20° C. and 50° C.

Compounds of formula (II), where R² and R³ are as defined above, may be prepared by reaction of a compound of formula (III),

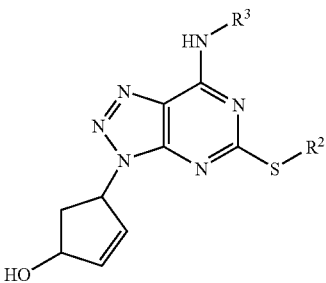

(III)

where R² and R³ are as defined above, by conversion of the hydroxyl group to an ester by treatment with an acylating agent, preferably acetyl chloride, in an inert solvent, preferably dichloromethane, in the presence of a base, preferably pyridine or 4-dimethylaminopyridine, at a temperature between 10° C. and 50° C. and then reductive removal of the ester function by treatment with a reducing agent, preferably sodium borohydride, in the presence of a Pd(0) catalyst, preferably tetrakis(triphenylphosphine)palladium(0), in an inert solvent, preferably tetrahydrofuran or a hindered alcohol.

Compounds of formula (III), where R² and R³ are as defined above, may be prepared by reaction of a compound of formula (IV),

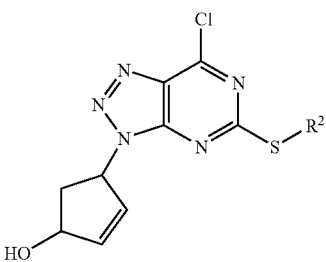

(IV)

where $R^2$ is defined above, with a compound of formula $R^3NH_2$, where $R^3$ is as defined above, in the presence of a base, preferably N,N-di-isopropylethylamine, in an inert solvent, preferably tetrahydrofuran or dichloromethane, at a temperature between 10° C. and 50° C.

Compounds of formula (IV), where $R^2$ is defined above, may be prepared by reaction of a compound of formula (V),

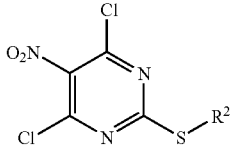

(V)

where $R^2$ is defined above, with 4-amino-2-cyclopenten-1-ol in an inert solvent, preferably tetrahydrofuran, in the presence of a base, preferably triethylamine, at a temperature between 10° C. and 50° C., and then reduction of the nitro group by treatment with an appropriate reducing agent, preferably a suspension of iron powder in an acidic solvent, preferably acetic acid, at a temperature between 10° C. and 50° C., followed by closure of the triazole ring by the use of a nitrosating agent, preferably iso-amyl nitrite, in an inert solvent, preferably acetonitrile, at a temperature between 20° C. and 90° C.

b) The reaction of a compound of formula (VI),

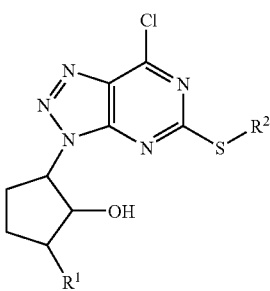

(VI)

where $R^1$ and $R^2$ are as defined above, with a compound of formula $R^3NH_2$, eg a compound of formula (VII),

(VII)

where $R^4$ is as defined above, in the presence of a base, preferably N,N-di-isopropylethylamine, in an inert ethereal solvent, preferably diethyl ether or tetrahydrofuran or a chlorocarbon solvent, preferably dichloromethane, at a temperature between 20° C. and 50° C.

Where $R^4$ is phenyl, (1R-trans)-2-phenylcyclopropanamine, [R-(R*,R*)]-2,3-dihydroxybutanedioate (1:1), the compound of formula (IV) may be prepared as described by L. A. Mitscher et al, J. Med. Chem., 1986, 29, 2044. Where $R^4$ is substituted phenyl, the compound of formula (VII) may be prepared as described in WO 9905143.

Compounds of formula (VI), where $R^1$ and $R^2$ are as defined above, may be prepared by reaction of a compound of formula (V), where $R^2$ is defined above, with a compound of formula (VIII), (VIII)

where $R^1$ is as defined above, in an inert solvent, preferably tetrahydrofuran, in the presence of a base, preferably triethylamine, at a temperature between 10° C. and 50° C., and reduction of the nitro group by treatment with an appropriate reducing agent, preferably a suspension of iron powder in an acidic solvent preferably acetic acid, at a temperature between 10° C. and 50° C., followed by closure of the triazole ring by the use of a nitrosating agent, preferably iso-amyl nitrite, in an inert solvent, preferably acetonitrile, at a temperature between 20° C. and 90° C.

c) The reaction of a compound of formula I, where $R^1$ and $R^2$ are as defined above, with an oxidising agent, preferably 3-chloroperoxybenzoic acid, in an inert solvent, preferably dichloromethane, at a temperature between 10° C. and 50° C., followed by reaction of the thus formed sulphonyl compound with a compound of formula $R^{2'}SM$, where $R^{2'}$ is a different group $R^2$ as defined above and M is a group I or II metal, preferably sodium, in an inert solvent, preferably tetrahydrofuran, at a temperature between 10° C. and 50° C.

All novel intermediates form a further aspect of the invention.

Salts of the compounds of formula (I) may be formed by reacting the free base, or a salt or a derivative thereof, with one or more equivalents of the appropriate acid (for example a hydrohalic (especially HCl), sulphuric, oxalic or phosphoric acid). The reaction may be carried out in a solvent or medium in which the salt is insoluble or in a solvent in which the salt is soluble, e.g. water, ethanol, tetrahydrofuran or diethyl ether, which may be removed in vacuo, or by freeze drying. The reaction may also be a metathetical process or it may be carried out on an ion exchange resin. The nontoxic physiologically acceptable salts are preferred, although other salts may be useful, e.g. in isolating or purifying the product.

The compounds of the invention act as $P_{2T}$ ($P2Y_{ADP}$ or $P2T_{AC}$) receptor antagonists. Accordingly, the compounds are useful in therapy, including combination therapy, particularly they are indicated for use as: inhibitors of platelet activation, aggregation and degranulation, promoters of platelet disaggregation, anti-thrombotic agents or in the treatment or prophylaxis of unstable angina, coronary revascularisation procedures including angioplasty (PTCA), myocardial infarction, perithrombolysis, primary arterial thrombotic complications of atherosclerosis such as thrombotic or embolic stroke, transient ischaemic attacks, peripheral vascular disease, myocardial infarction with or without thrombolysis, arterial complications due to interventions in atherosclerotic disease such as angioplasty, endarterectomy, stent placement, coronary and other vascular graft surgery, thrombotic complications of surgical or mechanical damage such as tissue salvage following accidental or surgical trauma, reconstructive surgery including skin and muscle flaps, conditions with a diffuse thrombotic/platelet consumption component such as disseminated intravascular coagulation, thrombotic thrombocytopaenic purpura, haemolytic uraemic syndrome, thrombotic complications of septicaemia, adult respiratory distress syndrome, anti-phospholipid syndrome, heparin-induced thrombocytopaenia and pre-eclampsia/eclampsia, or venous thrombosis such as deep vein thrombosis, venoocclusive disease, haematological conditions such as myeloproliferative disease, including thrombocythaemia, sickle cell disease; or in the prevention of mechanically-induced platelet activation in vivo, such as cardio-pulmonary bypass and extracorporeal membrane oxygenation (prevention of microthromboembolism), mechanically-induced platelet activation in vitro, such as use in the preservation of blood products, e.g. platelet concentrates, or shunt occlusion such as in renal dialysis and plasmapheresis, thrombosis secondary to vascular damage/inflammation such as vasculitis, arteritis, glomerulonephritis, inflammatory bowel disease and organ graft rejection, conditions such as migraine, Raynaud's phenomenon, conditions in which platelets can contribute to the underlying inflammatory disease process in the vascular wall such as atheromatous plaque formation/progression, stenosis/restenosis and in other inflammatory conditions such as asthma, in which platelets and platelet-derived factors are implicated in the immunological disease process. Further indications include treatment of CNS disorders and prevention of the growth and spread of tumours.

According to the invention there is further provided the use of a compound according to the invention as an active ingredient in the manufacture of a medicament for use in the treatment or prevention of the above disorders. In particular the compounds of the invention are useful for treating myocardial infarction, thrombotic stroke, transient ischaemic attacks, peripheral vascular disease and stable and unstable angina, especially unstable angina. The invention also provides a method of treatment or prevention of the above disorders which comprises administering a therapeutically effective amount of a compound according to the invention to a person suffering from or susceptible to such a disorder.

The compounds may be administered topically, e.g. to the lung and/or the airways, in the form of solutions, suspensions, HFA aerosols and dry powder formulations; or systemically, e.g. by oral administration in the form of tablets, pills, capsules, syrups, powders or granules, or by parenteral administration in the form of sterile parenteral solutions or suspensions, by subcutaneous administration, or by rectal administration in the form of suppositories or transdermally.

The compounds of the invention may be administered on their own or as a pharmaceutical composition comprising the compound of the invention in combination with a pharmaceutically acceptable diluent, adjuvant or carrier. Particularly preferred are compositions not containing material capable of causing an adverse, e.g. an allergic, reaction.

Dry powder formulations and pressurised HFA aerosols of the compounds of the invention may be administered by oral or nasal inhalation. For inhalation the compound is desirably finely divided. The compounds of the invention may also be administered by means of a dry powder inhaler. The inhaler may be a single or a multi dose inhaler, and may be a breath actuated dry powder inhaler.

One possibility is to mix the finely divided compound with a carrier substance, e.g. a mono-, di- or polysaccharide, a sugar alcohol or another polyol. Suitable carriers include sugars and starch. Alternatively the finely divided compound may be coated by another substance. The powder mixture may also be dispensed into hard gelatine capsules, each containing the desired dose of the active compound.

Another possibility is to process the finely divided powder into spheres, which break up during the inhalation procedure. This spheronized powder may be filled into the drug reservoir of a multidose inhaler, e.g. that known as the Turbuhaler® in which a dosing unit meters the desired dose which is then inhaled by the patient. With this system the active compound with or without a carrier substance is delivered to the patient.

The pharmaceutical composition comprising the compound of the invention may conveniently be tablets, pills, capsules, syrups, powders or granules for oral administration; sterile parenteral or subcutaneous solutions, suspensions for parenteral administration or suppositories for rectal administration.

For oral administration the active compound may be admixed with an adjuvant or a carrier, e.g. lactose, saccharose, sorbitol, mannitol, starches such as potato starch, corn starch or amylopectin, cellulose derivatives, a binder such as gelatine or polyvinylpyrrolidone, and a lubricant such as magnesium stearate, calcium stearate, polyethylene glycol, waxes, paraffin, and the like, and then compressed into tablets. If coated tablets are required, the cores, prepared as described above, may be coated with a concentrated sugar solution, which may contain e.g. gum arabic, gelatine, talcum, titanium dioxide, and the like. Alternatively, the tablet may be coated with a suitable polymer dissolved either in a readily volatile organic solvent or an aqueous solvent.

For the preparation of soft gelatine capsules, the compound may be admixed with e.g. a vegetable oil or polyethylene glycol. Hard gelatine capsules may contain granules of the compound using either the above mentioned excipients for tablets, e.g. lactose, saccharose, sorbitol, mannitol, starches, cellulose derivatives or gelatine. Also liquid or semisolid formulations of the drug may be filled into hard gelatine capsules.

Liquid preparations for oral application may be in the form of syrups or suspensions, for example solutions containing the compound, the balance being sugar and a mixture of ethanol, water, glycerol and propylene glycol. Optionally such liquid preparations may contain colouring agents, flavouring agents, saccharine and carboxymethylcellulose as a thickening agent or other excipients known to those skilled in art.

EXAMPLES

The invention is illustrated by the following non-limiting examples.

In the examples the NMR spectra were measured on a Varian Unity Inova 300 or 400 spectrometer and the MS spectra were measured as follows: EI spectra were obtained on a VG 70-250S or Finnigan Mat Incos-XL spectrometer, FAB spectra were obtained on a VG70-250SEQ spectrometer, ESI and APCI spectra were obtained on Finnigan Mat SSQ7000 or a Micromass Platform spectrometer. Preparative HPLC separations were generally performed using a Novapak®, Bondapak® or Hypersil® column packed with BDSC-18 reverse phase silica. Flash chromatography (indicated in the Examples as ($SiO_2$)) was carried out using Fisher Matrix silica, 35–70 μm. For examples which showed the presence of rotamers in the proton NMR spectra only the chemical shifts of the major rotamer are quoted.

Example 1

[1R-[1α,2α,3β(1R*,2S*)]]-3-[7-[(2-Phenylcyclopropyl)amino]-5-(propylthio)-3H-[1,2,3]triazolo[4,5-d]pyrimidin-3-yl]cyclopentane-1,2-diol a) (1S-cis)-4-[[6-Chloro-5-nitro-2-(propylthio)-pyrimidin-4-yl]amino]-2-cyclopenten-1-ol To a solution of 4,6-dichloro-5-nitro-3-propylthiopyrimidine (prepared as described in WO 9703084) (4.00 g) and triethylamine (2.00 ml) in dry tetrahydrofuran (100 ml) was added dropwise over 1 hour a solution of [1S-cis]-4-amino-2-cyclopenten-1-ol (prepared as described by S. F. Martin et al., Tetrahedron Lett., 1992, 33, 3583) (1.48 g) in a mixture of tetrahydrofuran (100 ml) and 1,4-dioxane (50 ml). The reaction mixture was filtered, concentrated in vacuo and the residue purified by chromatography (SiO$_2$, ethyl acetate:isohexane 1:4 to 1:1 as eluant) to afford the sub-title compound (3.18 g).

MS (APCI) 313 (M−H$_2$O+H$^+$, 100%).

b) (1S-cis)-4-[[5-Amino-6-chloro-2-(propylthio)pyrimidin-4-yl]amino]-2-cyclopenten-1-ol Iron powder (2.30 g) was added to a stirred solution of the product of step a) (2.61 g) in acetic acid (100 ml). The reaction mixture was stirred at room temperature for 2 hours, concentrated in vacuo to half volume, diluted with ethyl acetate and washed with water. The organic layer was dried and concentrated in vacuo to afford the sub-title compound (2.28 g).

NMR δH (d$_6$-DMSO) 7.03 (1H,d), 5.93–5.90 (1H, m), 5.85–5.82 (1H, m), 5.05(1H, d), 4.91–4.85 (2H, m), 4.66–4.60 (1H, m), 2.94 (2H, t), 2.77–2.68 (1H, m), 1.69–1.57 (2H, sextuplet), 1.48–1.42 (1H, quintuplet), 0.94 (3H, t).

c) (1S-cis)-4-[7-Chloro-5-(propylthio)-3H-[1,2,3]triazolo[4,5-d]pyrimidin-3-yl]-2-cyclopenten-1-ol Isoamyl nitrite (1.08 ml) was added to a solution of the product of step b) (2.20 g) in acetonitrile (100 ml) and the solution heated at 70° C. for 1 hour. The cooled reaction mixture was concentrated in vacuo and the residue purified by chromatography (SiO$_2$, ethyl acetate:isohexane 1:2 as eluant) to afford the subtitle compound (1.79 g).

MS (APCI) 312 (M+H$^+$), 224 (100%).

d) [1S-[1α,4α(1S*,2R*)]]-4-[7-[(2-Phenylcyclopropyl)amino]-5-(propylthio)-3H-[1,2,3]triazolo[4,5-d]pyrimidin-3-yl]-2-cyclopenten-1-ol A solution of the product from step (c) (0.65 g), (1R-trans)-2-phenyl-cyclopropanamine, [R-(R*,R*)]-2,3-dihydroxybutanedioate (1:1) (prepared as described by L. A. Mitscher et al., J. Med. Chem. 1986, 29, 2044) (0.65 g) and N,N-diisopropylethylamine (1.1 ml) in dichloromethane (20 ml) was stirred at room temperature for 16 hours. The reaction mixture was concentrated in vacuo and the residue purified by chromatography (SiO$_2$, ethyl acetate:hexane 1:2 as eluant) to afford the sub-title compound (0.786 g).

MS (APCI) 409 (M+H$^+$, 100%)

e) [1S-[1α,4α(1S*,2R*)]]-4-[7-[(2-Phenylcyclopropyl)amino]-5-(propylthio)-3H-[1,2,3]triazolo [4,5-d]pyrimidin-3-yl]-2-cyclopentene-1-ol, acetate (ester)

To a solution of the product of step d) (0.78 g), pyridine (0.43 ml) and 4-dimethylaminopyridine (1 mg) in dichloromethane (15 ml) was added acetyl chloride (0.16 ml). The solution was stirred for 3 hours and then concentrated in vacuo. The residue was purified by chromatography (SiO$_2$, ethyl acetate:hexane 1:1 as eluant) to afford the sub-title compound (0.75 g).

MS (APCI) 451 (M+H$^+$, 100%).

f) [1R-[1α(1R*,2S*)]]-3-(2-Cyclopenten-1-yl)-N-(2-phenylcyclopropyl)-5-(propylthio)-3H-[1,2,3]triazolo[4,5-d]pyrimidin-7-amine (and (1R-trans)-3-(3-cyclopenten-1-yl)-N-(2-phenylcyclopropyl)-5-(propylthio)-3H-[1,2,3]triazolo[4,5-d]pyrimidin-7-amine)

To a mixture of the product from step e) (0.50 g) and sodium borohydride (0.21 g) in tetrahydrofuran (10 ml) and 2-propanol (10 ml) was added tetrakis(triphenylphosphine)palladium(0) (6 mg). The reaction mixture was stirred for 10 minutes, concentrated in vacuo and the residue purified by chromatography (SiO$_2$, ethyl acetate:hexane 1:10 as eluant) to afford the sub-title compounds (0.38 g) as a 3:1 mixture that was used without further purification.

MS (APCI) 393 (M+H$^+$, 100%)

g) [1R-[1α,2α,3β(1R*,2S*)]]-3-[7-[(2-Phenylcyclopropyl)amino]-5-(propylthio)-3H-[1,2,3]triazolo[4,5-d]pyrimidin-3-yl]cyclopentane-1,2-diol To a mixture of the products from step f) (0.34 g), N-methylmorpholine-N-oxide (0.20 g), tetrahydrofuran (10 ml) and water (1 ml) was added osmium tetroxide (0.9 ml, 2.5% solution in t-butanol). The mixture was stirred at room temperature for 16 hours and then treated with sodium hydrosulphite (0.15 g) and water (1 ml). The suspension was filtered through Celite and the filtrate concentrated in vacuo. The residue was purified by chromatography (SiO$_2$, ethyl acetate:hexane 1:1 as eluant) to afford the title compound (0.14 g).

MS (APCI) 427 (M+H$^+$, 100%).

NMR δH (d$_6$-DMSO) 0.82 and 0.99 (3H, t), 1.21–1.76 (5H, m), 1.95–2.37 (4H, m), 2.80–3.10 (2H, m), 3.18–3.21 and 3.82–3.87 (1H, m), 4.04 (1H, m), 4.46 (1H, m), 4.76 (1H, d), 5.01–5.05 (2H, m), 7.16–7.21 (3H, m), 7.27–7.31 (2H, m), 9.33 (1H, d).

Example 2

[1R-[1α,2α,3β(1R*,2S*)]]-3-[7-[[2-(4-Methylphenyl)cyclopropyl]amino]5-(propylthio)-3H-[1,2,3]triazolo[4,5-d]pyrimidin-3-yl]cyclopentane-1,2-diol a) (3R)-3-[Bis[(1,1-dimethylethoxy)carbonyl]amino]-1-cyclopentene To a solution of (1S-cis)-4-(di-tert-butoxycarbonylamino)cyclopent-2-enyl acetate (prepared as described by D. Zhang et.al. Tett. Lett. 1996, 3799–3802) (8.98 g), tetrakis(triphenylphosphine)palladium(0) (0.463 g) in isopropanol (135 ml) and tetrahydrofuran (135 ml) was added sodium borohydride (4.97 g) portionwise at 0° C. The mixture was stirred at 0° C. for 3 hours before the careful dropwise addition of glacial acetic acid (20 ml). The solution was concentrated in vacuo and the residue purified by chromatography (SiO$_2$, diethylether 1:9 isohexane as eluent) to afford the sub-title compound (5.90 g).

NMR δH (CDCl$_3$) 5.82 (1H, m), 5.70–5.61 (2H, m), 5.20 (1H, m), 2.65–1.85 (3H, m), 1.49–1.48 (18H, s).

b) [1R-(1α,2α,3β)]-1-[Bis[(1,1-dimethylethoxy)carbonyl]amino]-2,3-dihydroxycyclopentane To a mixture of the product from step a) (5.90 g), N-methylmorpholine-N-oxide (3.19 g), tetrahydrofuran (150 ml) and water (15 ml) was added osmium tetraoxide (10.60 ml, 2.5% solution in t-butanol). The mixture was stirred at room temperature for 16 hours and then treated with sodium hydrosulphite (3.50 g) and water (50 ml). The suspension was filtered through Celite and the filtrate concentrated in vacuo. The residue was purified by chromatography (SiO$_2$, ethyl acetate: hexane 1:2 as eluant) to afford the sub-title compound (4.135 g).

NMR δH (d$_6$-DMSO) 4.55–4.41 (2H, m), 4.34–4.08 (2H, m), 3.83–3.81 (1H, m), 1.90–1.47 (4H, m), 1.44 (18H, s).

c) [1R-(1α,2α,3β)]-3-Aminocyclopentane-1,2-diol, hydrochloride

To a solution of product from step b) (4.1 g) in methanol (40 ml) was added conc. hydrochloric acid (10 ml). The solution was stirred for 4 hours and concentrated in vacuo to give an oil, which was azeotroped with toluene to afford the sub-title compound (3.10 g).

NMR δH (d$_6$-DMSO) 8.28 (2H, s), 4.63 (3H, s), 3.91–3.78 (2H, m), 3.26–3.20 (1H, m), 2.10–1.80 (2H, m), 1.52–1.49 (2H, m).

d) [1R-(1α,2α,3β)]-3-[[6-Chloro-5-nitro-2-(propylthio)-pyrimidin-4-yl]amino]cyclopentane-1,2-diol A solution of the product from step c) (3.10 g) in dry tetrahydrofuran (100 ml) was added dropwise over 1 hour to a solution of 4,6-dichloro-5-nitro-3-propylthiopyrimidine (prepared as described in WO 9703084) (7.00 g) and N,N-diisopropylethylamine (11.30 ml) in dry tetrahydrofuran (100 ml). The reaction mixture was heated to reflux for 20 hours and concentrated in vacuo. The residue was purified by chromatography (SiO$_2$, ethyl acetate:isohexane 1:1 as eluant) to afford the sub-title compound (3.79 g)

NMR δH (CDCl$_3$) 7.97–7.95 (1H, d), 4.48–4.43 (1H, m), 4.18–4.08 (2H, d), 3.94–3.91 (1H, m), 3.18–3.08 (2H, m), 2.50–2.43 (1H, m), 2.09–2.07 (1H, m), 1.90–1.87 (1H, m), 1.81–1.73 (2H, q), 1.60–1.54 (2H, m), 1.08–1.03 (3H, t).

e) [1R-(1α,2α,3β)]-3-[[5-Amino-6-chloro-2-(propylthio)-pyrimidin-4-yl]amino]cyclopentane-1,2-diol Iron powder (3.80 g) was added to a stirred solution of the product of step d) (3.80 g) in acetic acid (50 ml). The reaction mixture was stirred at room temperature for 2 hours, concentrated in vacuo to half volume, diluted with ethyl acetate and washed with water. The organic layer was dried and concentrated in vacuo to afford the sub-title compound (3.36 g).

MS (APCI) 319 (M+H$^+$) (100%).

f) [1R-(1α,2α,3β)]-3-[7-Chloro-5-(propylthio)-3H-[1,2,3]triazolo[4,5-d]pyrimidin-3-yl]cyclopentane-1,2-diol A solution of sodium nitrite (1.23 g) in water (5 ml) was added dropwise to solution of product from step e) (3.36 g) in acetic acid (50 ml). The reaction mixture was stirred at room temperature for 2 hours and concentrated in vacuo. The residue purified by chromatography (SiO$_2$, ethyl acetate:isohexane 1:1 as eluant) to afford the sub-title compound (2.20 g).

MS (APCI) 302 (M+H$^+$) loss of N$_2$ (100%).

NMR δH (CDCl$_3$) 5.27–5.18 (1H, m), 4.69–4.65 (1H, m), 4.42–4.38 (1H, m), 3.21–3.16 (2H, t), 2.69–2.59 (1H, m), 2.39–2.26 (2H, m), 2.09–1.98 (1H, m), 1.87–1.75 (2H, m), 1.11–1.06 (3H, t).

g) [1R-[1α,2α,3β(1R*,2S*)]]-3-[7-[[2-(4-Methylphenyl)cyclopropyl]amino]-5-(propylthio)-3H-[1,2,3]triazolo[4,5-d]pyrimidin-3-yl]cyclopentane-1,2-diol A solution of the product from step f) (0.150 g), (1R-trans)-2-(4-methylphenyl)cyclopropanamine, [R-(R*,R*)]-2,3-dihydroxybutanedioate (1:1) (prepared as described WO 9905143) (0.65 g) and N,N-diisopropylethylamine (0.155 ml) in dioxane (20 ml) was stirred at room temperature for 16 hours. The reaction mixture was concentrated in vacuo and the residue purified by chromatography (SiO$_2$, ethyl acetate:dichloromethane 1:2 as eluant) to afford the sub-title compound (0.120 g).

MS (APCI) 441 (M+H$^+$, 100%)

NMH δH (d$_6$-DMSO) 9.30–9.29 (1H, d), 7.08–7.05 (4H, s), 5.06–4.75 (3H, m), 4.49–4.42 (1H, m), 4.05 (1H, m), 3.16–2.86 (3H, m), 2.26 (3H, s), 2.12–1.97 (3H, m), 1.73–1.26 (3H, m), 0.85–0.80 (3H, t)

Example 3

[1R-[1α,2α,3β(1R*,2S*)]]-3-[7-[-2-Phenylcyclopropyl)amino]-5-(methylthio)-3H-[1,2,3]triazolo[4,5-d]pyrimidin-3-yl]cyclopentane-1,2-diol a) [1R-[1α,2α,3β(1R*,2S*)]]-3-[7-[(2-Phenylcyclopropyl)amino]-5-(propylthio)-3H-[1,2,3]triazolo[4,5-d]pyrimidin-3-yl]cyclopentane-1,2-diol The title compound was prepared as described in Example 1, step d) using (1R-trans)-2-phenylcyclopropanamine and the product from Example 2, step f).

MS (APCI) 427 (M+H$^+$, 100%).

b) [1R-[1α,2α,3β(1R*,2S*)]]-3-[7-[(2-Phenylcyclopropyl)amino]-5-(propylsulphonyl)-3H-[1,2,3]triazolo[4,5-d]pyrimidin-3-yl]cyclopentane-1,2-diol A solution of product from step a) (1.50 g) in dichloromethane was treated with 3-chloroperoxybenzoic acid (2.42 g). The solution was stirred at room temperature for 2 hours before washing organic layer with sodium metabisulphite solution. The organic layer was dried (MgSO$_4$) and concentrated in vacuo. The residue was purified by chromatography (SiO$_2$, ethyl acetate as eluant) to afford the sub-title compound (1.30 g).

MS (APCI) 459 (M+H$^+$, 100%).

c) [1R-[1α,2α,3β(1R*,2S*)]]-3-[7-[(2-Phenylcyclopropyl)amino]-5-(methylthio)-3H-[1,2,3]triazolo[4,5-d]pyrimidin-3-yl]cyclopentane-1,2-diol A solution of product from step b) (0.15 g) in tetrahydrofuran (10 ml) was treated with sodium methanethiolate (0.046 g) in water (1 ml). The solution was stirred at room temperature overnight. The solution was concentrated in vacuo and residue was purified by chromatography (SiO$_2$, ethyl acetate:dichloromethane 1:1 as eluant) to afford the title compound (0.095 g).

MS (APCI) 399 (M+H$^+$, 100%).

NMR δH (d$_6$-DMSO) 7.34–7.19 (5H, m), 6.66–5.68 (2H, s), 5.02–4.99 (1H, m), 4.50–4.34 (2H, m), 3.20 (1H, m), 2.73–2.68 (1H, m), 2.40 (4H, m), 2.29–2.19 (2H, m), 2.05–2.00 (1H, m), 1.44–1.26 (2H, m)

Example 4

[1R-[1α,2α,3β(1R*,2S*)]]-3-[7-[(2-Phenylcyclopropyl)amino]-5-(ethylthio)-3H-[1,2,3]triazolo[4,5-d]pyrimidin-3-yl]cyclopentane-1,2-diol a) [1R-[1α,2α,3β(1R*,2S*)]]-3-[7-[(2-Phenylcyclopropyl)amino]-5-(ethylthio)-3H-[1,2,3]triazolo[4,5-d]pyrimidin-3-yl]cyclopentane-1,2-diol A solution of product from Example 3, step b) (0.15 g) in tetrahydrofuran (10 ml) was treated with sodium ethanethiolate (0.055 g) in water (1 ml) and the reaction mixture stirred at room temperature overnight. The solution was concentrated in vacuo and residue purified by chromatography (SiO$_2$, ethyl acetate:dichloromethane 1:1 as eluant) to afford the title compound (0.06 g).

MS (APCI) 413 (M+H$^+$, 100%).

NMR δH (d$_6$-DMSO) 7.34–7.20 (5H, m), 6.66 (1H, s), 5.55 (1H, s), 5.05–4.96 (1H, m), 4.50–4.35 (2H, m), 3.22–2.38 (5H, m), 2.30–2.20 (2H, m), 2.05–1.95 (1H, m), 1.43–1.17 (5H, m).

Example 5

[1R-(1α,2α,3β)]-3-[7-(Cyclopropylamino)-5-(propylthio)-3H-[1,2,3]triazolo[4,5-d]pyrimidin-3-yl]cyclopentane-1,2-diol The title compound was prepared using the product from Example 2, step f) and cyclopropanamine as described in Example 1, step d).

MS (APCI) 351 (M+H$^+$, 100%)

NMR δH(d$_6$-DMSO) 9.06–9.04 (1H, m), 5.04–4.75 (3H, m), 4.49–4.42 (1H, m), 4.05 (1H, m), 3.12–3.04 (3H, m), 2.37–1.98 (3H, m), 1.76–1.67 (3H, m), 1.01–0.96 (3H, t), 0.87–0.67 (3H,m).

Example 6

[1R-(1α,2α,3β)]-3-[7-(Cyclopropylamino)-5-(3,4-dichlorophenylthio)-3H-[1,2,3]triazolo[4,5-d]pyrimidin-3-yl]cyclopentane-1,2-diol a) [1R-(1α,2α,3β)]-3-[7-(Cyclopropylamino)-5-(propylsulphonyl)-3H-[1,2,3]triazolo[4,5-d]pyrimidin-3-yl]cyclopentane-1,2-diol The title compound was prepared using the product from Example 5 as described in Example 3, step b).

MS (APCI) 383 (M+H$^+$, 100%).

b) [1R-(1α,2α,3β)]-3-[7-(Cyclopropylamino)-5-(3,4-dichlorophenylthio)-3H-[1,2,3]triazolo[4,5-d]pyrimidin-3-yl]cyclopentane-1,2-diol The title compound was prepared using the product from step a) and 3,4-dichlorothiophenol as described in Example 3, step c) but with 60% NaH in N,N-dimethylformamide (10 ml).

MS (APCI) 453 (M+H$^+$, 100%).

NMR δH (d$_6$-DMSO) 9.22–9.20 (1H, d), 7.97–7.56 (3H, m), 4.98–4.71 (3H, m), 4.31–3.84 (2H, m), 2.92–2.89 (1H, m), 2.20–2.18 (1H, m), 1.84–1.54 (4H, m), 0.88–0.87 (1H, m), 0.69–0.63 (3H,m).

Example 7

[1R-(1α,2α,3β)]-3-[7-(Cyclopropylamino)-5-(4-trifluoromethylphenylthio)-3H-[1,2,3]triazolo [4,5-d]pyrimidin-3-yl]cyclopentane-1,2-diol The title compound was prepared using the product from Example 6, step a) and 4-trifluoromethylthiophenol as described in Example 6, step b).

MS (APCI) 453 (M+H$^+$, 100%).

NMR δH (d$_6$-DMSO) 9.20–9.19 (1H, m), 7.90–7.79 (4H, m), 5.04–4.89 (2H, m), 4.69–4.65 (1H, m), 4.28–4.21 (1H, m), 3.83–3.78 (1H, m), 2.94–2.88 (1H, m), 2.27–2.13 (1H, m), 1.82–1.80 (1H,m), 1.51 (1H, m), 0.67–0.65 (3H, t).

Example 8

[1R-[1α,2α,3β(1R*,2S*)]]-3-[7-[(2-Phenylcyclopropyl)amino]-5-(butylthio)-3H-1,2,3-triazolo[4,5-d]pyrimidin-3-yl]cyclopentane-1,2-diol To a suspension of NaH (28 mg) in tetrahydrofuran (10 ml) was added butanethiol (63 mg), after 10 minutes the product from Example 3 step b) (200 mg) was added in tetrahydrofuran (1 ml). The mixture was stirred for 12 hours before addition of saturated brine (25 ml), the organic products were extracted into ethyl acetate (2×25 ml), dried (MgSO$_4$) and concentrated to an oil. The residue was purified by chromatography (SiO$_2$, methanol:dichloromethane 1:25 as eluant) to afford the title compound (0.087 g).

MS (APCI) 441 (M+H$^+$, 100%).

NMR δH (d$_6$-DMSO) 9.32 (1H, d), 7.29 (2H, m), 7.18 (3H, m), 5.00 (2H, m), 4.75 (1H, d), 4.47 (1H, m), 4.05 (1H, m), 3.20 (1H, m), 2.80–3.00 (2H, m), 2.30 (2H, m), 1.90–20 (3H, m), 1.71 (1H, m), 1.41 (2H, m), 1.32 (2H, m), 0.81 (3H, t).

Example 9

[1R-[1α,2α,3β(1R*,2S*)]]-3-[7-[(2-Phenylcyclopropyl)amino]-5-(3,3,3-trifluoropropylthio)-3H-1,2,3-triazolo [4,5-d]pyrimidin-3-yl]cyclopentane-1,2-diol The title compound was prepared as described in Example 8 using the product from Example 3, step b) and 3,3,3-trifluoropropanethiol

MS (APCI) 481 (M+H$^+$, 100%).

NMR δH (d$_6$-DMSO) 7.10–7.30 (5H, m), 5.03 (2H, m), 4.76 (1H, d), 4.47 (1H, m), 4.00 (1H, m), 3.05–3.20 (3H, m), 2.50 (2H, m), 2.00–2.35 (m, 4H), 1.70 (1H, m), 1.45 (1H, m), 1.27 (1H, m).

Example 10

[1R-[1α,2α,3β(1R*,2S*)]]-3-[7-[[2-(4-Chlorophenyl)cyclopropyl]amino]-5-(butylthio)-3H-1,2,3-triazolo[4,5-d]pyrimidin-3-yl]cyclopentane-1,2-diol a) [1R-1α,2α,3β(1R*,2S*)1-3-[7-[2-(4-Chlorophenyl)cyclopropyl]amino]-5-(propylylthio)-3H-1,2,3-triazolo[4,5-d]pyrimidin-3-yl]cyclopentane-1,2-diol The subtitle compound was prepared as described in Example 2, step g) using the product from Example 2, step f) and 2-(4-chlorophenyl)cyclopropanamine (prepared as described in WO 9905143).

MS (APCI) 461 (M+H$^+$, 100%).

b) [1R-[1α,2α,3β(1R*,2S*)]]-3-[7-[[2-(4-Chlorophenyl)cyclopropyl]amino]-5-(propylsulphonyl)-3H-1,2,3-triazolo[4,5-d]pyrimidin-3-yl]cyclopentane-1,2-diol The subtitle compound was prepared as described in Example 3, step b) using the product from Example 10, step a).

MS (APCI) 493 (M+H$^+$, 100%)

c) [1R-[1α,2α,3β(1R*,2S*)]]-3-[7-[[2-(4-Chlorophenyl)cyclopropyl]amino]-5-(butylthio)-3H-1,2,3-triazolo[4,5-d]pyrimidin-3-yl]cyclopentane-1,2-diol The title compound was prepared as described in Example 8 using the product from step b) and butanethiol.

MS (APCI) 475 (M+H$^+$, 100%).

NMR δH (d$_6$-DMSO) 9.35 (1H, d), 7.30 (2H, d), 7.20 (3H, m), 5.03 (2H, m), 4.80 (1H, m), 4.42 (1H, m), 4.05 (1H, m), 3.10–3.20 (1H, m), 2.90 (2H, m), 2.20–2.40 (1H, m), 2.00–2.19 (2H, m), 1.20–1.80 (8H, m), 0.81 (3H, t).

Example 11

[1R-[1α,2α,3β(1R*,2S*)]]-3-[7-[[2-(4-Fluorophenyl)cyclopropyl]amino]-5(butylthio)-3H-1,2,3-triazolo[4,5-d]pyrimidin-3-yl]cyclopentane-1,2-diol a) [1R-[1α,2α,3β(1R*,2S*)]]-3-[7-[[2-(4-Fluorophenyl)cyclopropyl]amino]-5-(propylthio)-3H-1,2,3-triazolo[4,5-d]pyrimidin-3-yl]cyclopentane-1,2-diol The subtitle compound was prepared as described in Example 2 step g) using the product from Example 2, step f) and 2-(4-fluorophenyl)cyclopropylamine (prepared as described in WO 9905143).

MS (APCI) 445 (M+H$^+$, 100%).

b) [1R-[1α,2α,3β(1R*,2S*)]]-3-[7-[[2-(4-Fluorophenyl)clopropyl]amino]-5-(propylsulphonyl)-3H-1,2,3-triazolo[4,5-d]pyrimidin-3-yl]cyclopentane-1,2-diol The subtitle compound was prepared as described in Example 3, step b) using the product from step a).

MS (APCI) 477 (M+H$^+$, 100%)

c) [1R-[1α,2α,3β(1R*,2S*)]]-3-[7-[[2-(4-Fluorophenyl)clopropyl]amino]-5-(butylthio)-3H-1,2,3-triazolo[4,5-d]pyrimidin-3-yl]cyclopentane-1,2-diol The title compound was prepared as described in Example 8 using the product from step b) and butanethiol

MS (APCI) 459 (M+H$^+$, 100%).

NMR δH (d$_6$-DMSO) 9.32 (1H, d), 7.25 (2H, m), 7.11 (2H, t), 5.10 (2H, m), 4.77 (1H, d), 4.42 (1H, m), 4.08 (1H, s), 3.16 (1H, m), 2.80–3.00 (2H, m), 2.30 (1H, m), 2.17 (1H, d), 2.04 (1H, m), 1.70 (1H, m), 1.40–1.60 (3H, m), 1.20–1.40 (3H, m), 0.81 (3H, t).

Example 12

[1R-[1α,2β(1R*,2S*)]]-2-[7-[(2-Phenylcyclopropyl)amino]-5-(propylthio)-3H-[1,2,3]triazolo[4,5-d]pyrimidin-3-yl]cyclopentanol a) (trans)-2-Aminocyclopentanol To a solution of cyclopentane oxide (5 g) in ethanol (5 ml) was added 0.88 ammonia (5 ml) and the mixture heated at reflux for 9 hours. The solution was diluted with water (100 ml), extracted with ether (3×50 ml), the organic phases were combined, washed with saturated brine (2×50 ml), dried (MgSO$_4$) and evaporated in vacuo to afford the sub-title compound as an oily solid (8.1 g) that was used without further purification.

b) (trans)-2-[[6-Chloro-5-nitro-2-(propylthio)pyrimidin-4-yl]amino]cyclopentanol The sub-title compound (3.26 g) was prepared using the product from step a) (8.1 g) and 4,6-dichloro-5-nitro-3-propylthiopyrimidine (prepared as described in WO 9703084) (20 g) as described in Example 1, step a) to afford the sub-title compound.

MS (APCI) 330 (M+H$^+$, 94%).

c) (trans)-2-[7-Chloro-5-(propylthio)-3H-[1,2,3]triazolo[4,5-d]pyrimidin-3-yl]cyclopentanol The sub-title compound (2.63 g) was prepared using the product from step b) (3.8 g) as described in Example 1, step b).

MS (APCI) 314 (M+H$^+$, 95%)

d) [(trans)-2(1R-2S)1-2-[7-1(2-Phenylcyclopropyl)amino]-5-(propylthio)-3H-[1,2,3]triazolo[4,5-d]pyrimidin-3-yl]cyclopentanol (mixture of diastereomers)

The title compounds as a mixture of diastereomers (0.36 g) were prepared using the product from step c) (0.5 g) and (1R-trans)-2-phenylcyclopropanamine, [R-(R*,R*)]-2,3-dihydroxybutanedioate (1:1) (Prepared as described by L. A. Mitscher et al, J. Med. Chem., 1986, 29, 2044) (0.45 g) and N,N-diisopropylethylamine (0.55 ml) as described in Example 1, step d).

MS (APCI) 441 (M+H$^+$, 100%).

e) [1R-[1α,2β(1R*,2S*)]]-2-[7-[(2-Phenylcyclopropyl)amino]-5-(propylthio)-3H-[1,2,3]triazolo[4,5-d]pyrimidin-3-yl]cyclopentanol The diastereomers from step d) (0.3 g) were separated using supercritical fluid chromatography (Gilson SF3, Chiralpak AD column®, 3000 psi, ethanol:carbon dioxide. 35:65 as solvent) to give the to give the title compound (0.1 g) (and the[1S-[1α,2β(1S*,2R*)]]diastereomer).

MS (APCI) 441 (M+H$^+$, 100%).

NMR δH (d$_6$-DMSO) 0.82 (3H,t); 1.31–2.14 (11H, m); 2.82–2.94 (2H,m); 3.18–3.22 (1H, m); 4.53 (1H, t); 4.79–4.86 (1H, q); 5.14–5.19 (1H,d); 7.15–7.31 (5H, m); 6.33–6.16 (1H, d).

Example 13

[1R-[1α,2β(1R*,2S*)]]-2-[[7-[2-(4-Methoxyphenyl)cyclopropyl]amino]-5(propylthio)-3H-[1,2,3]triazolo[4,5-d]pyrimidin-3-yl]cyclopentanol a) (1R-trans)-2-[[5-Amino-6-chloro-2-(propylthio)-4-pyrimidinyl]amino]cyclopentanol A mixture of (1R-trans)-2-aminocyclopentanol (prepared as described in A. A. Barr et al., Can. J. Chem., 1997, 55, 4180) (3.0 g) and 4,6-dichloro-3-(propylthio)pyrimidin-5-amine (6.1 g) (prepared as described in EP 508687) in n-butanol (100 ml) containing N,N-diethylisopropylamine (10 ml) was heated at 100° C. for 8 hours. The reaction mixture was evaporated to dryness and the residue taken up into 2N hydrochloric acid (300 ml), washed with ether (100 ml) and then neutralised with 0.88 ammonia solution, to afford the sub-title compound (4.0g).

MS (APCI) 303 (M+H$^+$, 100%).

b) (1R-trans)-2-[7-Chloro-5-(propylthio)-3H-[1,2,3]triazolo[4,5-d]pyrimidin-3-yl]cyclopentanol Prepared using the product of step a) (4.0 g) by the method of Example 1 step c). Purified by chromatography (SiO$_2$, ethyl acetate:dichloromethane 1:9 as eluant) to afford the sub-title compound (4.1 g).

MS (APCI) 314 (M+H$^+$, 100%)

(c) [1R-[1α,2β(1R*,2S*)]]-2-[7-[[2-(4-Methoxyphenyl)cyclopropyl]amino]-5-(propylthio)-3H-[1,2,3]triazolo[4,5-d]pyrimidin-3-yl]cyclopentanol Prepared using the product from step b) (0.15 g) and (1R,2S)-2-(4-methoxyphenyl)cyclopropanamine, (2R,3R)-2,3-dihydroxybutanedioate (1:1) (0.20 g) (prepared as described in WO 9905143) by the method of Example 1, step d). Purified by chromatography (SiO$_2$, ethyl acetate: dichloromethane 1:9 as eluant) to afford the title compound (0.12 g).

MS (APCI) 441 (M+H$^+$, 100%).

NMR δH (d$_6$-DMSO) 9.28 (1H, d), 7.15 (2H, d), 6.84–6.86 (2H, d), 5.19 (1H, d), 4.83 (1H, m), 4.55 (1H, m), 3.72 (3H, s), 3.11 (1H, m), 2.90–2.97 (2H, m), 2.23 (1H, m), 2.11–2.23 (2H, m), 1.87 (2H, m), 1.67 (2H, m), 1.57 (2H, m), 1.42 (1H, m), 1.23 (1H, m), 0.84 (3H, t).

Example 14

[1R-[1α,2β(1R*,2S*)]]-2-[7-[[2-(3,4-Difluorophenyl)cyclopropyl]amino]-5-(propylthio)-3H-[1,2,3]triazolo[4,5-d]pyrimidin-3-yl]cyclopentanol Prepared using the product from Example 13 step b) (0.15 g) and (1R,2S)-2-(3,4-difluorophenyl)cyclopropanamine, (2R,3R)-2,3-dihydroxybutanedioate (1:1) (0.20 g) (prepared as described in WO 9905143) by the method of Example 13, step c). Purified by chromatography (SiO$_2$, ethyl acetate:dichloromethane 1:9 as eluant) to afford the title (0.12 g).

MS (APCI) 447 (M+H$^+$, 100%).

NMR δH (d$_6$-DMSO) 9.34 (1H, d), 7.27–7.38 (2H, m), 7.07 (1H, m), 5.18 (1H, d), 4.81 (1H, q), 4.51 (1H, t), 3.13–3.15 (1H, m), 2.83–2.95 (2H, m), 2.23–2.27 (1H, m), 2.07–2.17 (2H, m), 1.83–1.91 (2H, m), 1.61–1.68 (2H, m), 1.41–1.57 (3H, m), 1.38–1.40 (1H, m), 0.81 (3H, t).

Pharmacological Data

The preparation for the assay of the P$_{2T}$ (P2Y$_{ADP}$ or P2T$_{AC}$) receptor agonist/antagonist activity in washed human platelets for the compounds of the invention was carried out as follows.

Human venous blood (100 ml) was divided equally between 3 tubes, each containing 3.2% trisodium citrate (4 ml) as anti-coagulant. The tubes were centrifuged for 15 minutes at 240G to obtain a platelet-rich plasma (PRP) to which 300 ng/ml prostacyclin was added to stabilize the platelets during the washing procedure. Red cell free PRP was obtained by centrifugation for 10 minutes at 125G followed by further centrifugation for 15 minutes at 640G. The supernatant was discarded and the platelet pellet resuspended in modified, Calcium Free Tyrode solution (10 ml) (CFT), composition: NaCl 137 mM, NaHCO$_3$ 11.9 mM, NaH$_2$PO$_4$ 0.4 mM, KCl 2.7 mM, MgCl$_2$ 1.1 mM, dextrose 5.6 mM, gassed with 95% 0$_2$/5% CO$_2$ and maintained at 37° C. Following addition of a further 300 ng/ml PGI$_2$, the pooled suspension was centrifuged once more for 15 minutes at 640G. The supernatant was discarded and the platelets resuspended initially in 10 ml CFT with further CFT added to adjust the final platelet count to 2×10$^5$/ml. This final suspension was stored in a 60 ml syringe at 3° C. with air excluded. To allow recovery from PGI$_2$-inhibition of normal function, platelets were used in aggregation studies no sooner than 2 hours after final resuspension.

In all studies, 3 ml aliquots of platelet suspension were added to tubes containing CaCl$_2$ solution (60 μl of 50 mM solution with a final concentration of 1 mM). Human fibrinogen (Sigma, F 4883) and 8-sulphophenyltheophylline (8-SPT which was used to block any P$_1$-agonist activity of compounds) were added to give final concentrations of 0.2 mg/ml (60 μl of 10 mg/ml solution of clottable protein in saline) and 300 nM (10 μl of 15 mM solution in 6% glucose), respectively. Platelets or buffer as appropriate were added in a volume of 150 μl to the individual wells of a 96 well plate. All measurements were made in triplicate in platelets from each donor.

The agonist/antagonist potency was assessed as follows

Aggregation responses in 96 well plates were measured using the change in absorbance given by the plate reader at 660 nm. Either a Bio-Tec Ceres 900C or a Dynatech MRX was used as the plate reader.

The absorbance of each well in the plate was read at 660 nm to establish a baseline figure. Saline or the appropriate solution of test compound was added to each well in a volume of 10 μl to give a final concentration of 0, 0.01, 0.1, 1, 10 or 100 mM. The plate was then shaken for 5 minutes on an orbital shaker on setting 10 and the absorbance read at 660 nm.

Aggregation at this point was indicative of agonist activity of the test compound. Saline or ADP (30 mM; 10 μl of 450 mM) was then added to each well and the plate shaken for a further 5 minutes before reading the absorbance again at 660 nm.

Antagonist potency was estimated as a % inhibition of the control ADP response to obtain an IC$_{50}$. Compounds exemplified have pIC$_{50}$ values of more than 5.0.

The invention claimed is:

1. A compound of formula (I):

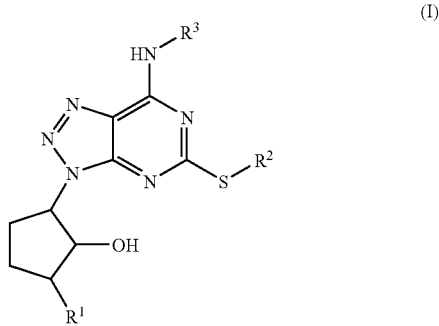

a pharmaceutically acceptable salt thereof, wherein:
R$^1$ is hydrogen or hydroxy;
R$^2$ is C$_{1-6}$ alkyl, or C$_{1-6}$ haloalkyl, or phenyl optionally substituted by halogen or by C$_{1-6}$ alkyl, optionally substituted by halogen;
R$^3$ is C$_{3-6}$ cycloalkyl, optionally substituted by R$^4$;
R$^4$ is hydrogen or phenyl, optionally substituted by C$_{1-6}$ alkyl, halogen, or C$_{1-6}$ alkoxy.

2. A compound according to claim 1 which is:

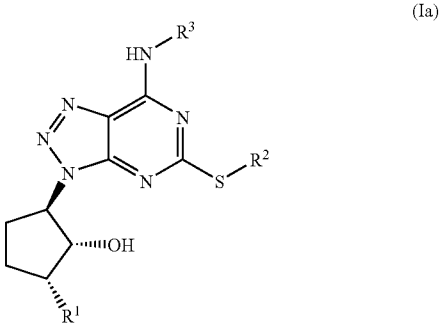

where R$^1$, R$^2$ and R$^3$ are as defined in claim 1.

3. A compound according to claim 2 in which $R^3$ where $R^3$ is

wherein $R^4$ is hydrogen or phenyl, optionally substituted by $C_{1-6}$ alkyl, halogen, or $C_{1-6}$ alkoxy.

4. A compound according to claim 1 in which $R^2$ is $C_{1-4}$ alkyl, or $C_{1-4}$ haloalkyl, or phenyl, optionally substituted by halogen, or by $C_{1-4}$ alkyl, optionally substituted by halogen.

5. A compound according to claim 3 in which $R^2$ is $C_{1-4}$ alkyl, or $C_{1-4}$ haloalkyl, or phenyl, optionally substituted by halogen, or by $C_{1-4}$ alkyl, optionally substitued by halogen.

6. A compound according to claim 1, in which $R^3$ is cyclopropyl, optionally substituted by $R^4$.

7. A compound according to claim 4, in which $R^3$ is cyclopropyl, optionally substituted by $R^4$.

8. A compound according to claim 5, in which $R^3$ is cyclopropyl, optionally substituted by $R^4$.

9. A compound according to claim 1, in which $R^4$ is hydrogen or phenyl, optionally substituted by halogen or $C_{1-4}$ alkoxy.

10. A compound according to claim 3, in which $R^4$ is hydrogen or phenyl, optionally substituted by halogen or $C_{1-4}$ alkoxy.

11. A compound according to claim 5, in which $R^4$ is hydrogen or phenyl, optionally substituted by halogen or $C_{1-4}$ alkoxy.

12. A compound according to claim 8, in which $R^4$ is hydrogen or phenyl, optionally substituted by halogen or $C_{1-4}$ alkoxy.

13. A compound according to claim 1 which is:
[1R-[1α,2α,3β(1R*,2S*)]]-3-[7-[(2-Phenylcyclopropyl) amino]-5-(propylthio)-3H-[1,2,3]triazolo[4,5-d]pyrimidin-3-yl]cyclopentane-1,2-diol;
[1R-[1α2,α3β(1R*,2S*)]]-3-[7-[[2-(4-Methylphenyl)cyclopropyl]amino-]-5-(propylthio)-3H-[1,2,3]triazolo[4,5-d]pyrimidin-3-yl]cyclopentane-1,2-diol;
[1R-[1α,2α,3β(1R*,2S*)]]-3-[7-[(2-Phenylcyclopropyl) amino]-5-(methylthio)-3H-[1,2,3]triazolo[4,5-d]pyrimidin-3-yl]cyclopentane-1,2-diol;
[1R-[1α,2α,3β(1R*,2S*)]]-3-[7-[(2-Phenylcyclopropyl) amino]-5-(ethylthio)-3H-[1,2,3]triazolo[4,5-d]pyrimidin-3-yl]cyclopentane-1,2-diol;
[1R-(1α,2α,3β)]-3-[7-(Cyclopropylamino)-5-(propylthio)-3H-[1,2,3]triazolo[4,5-d]pyrimidin-3-yl]cyclopentane-1,2-diol;
[1R-(1α,2α,3β)]-3-[7-(Cyclopropylamino)-5-(3,4-dichlorophenylthio)-3H-[1,2,3]triazolo[4,5-d]pyrimidin-3-yl]cyclopentane-1,2-diol;
[1R-(1α,2α,3β)]-3-[7-(Cyclopropylamino)-5-(4-trifluoromethylphenylthio)-3H-[1,2,3]triazolo[4,5-d]pyrimidin-3-yl]cyclopentane-1,2-diol;
[1R-[1α,2α,3β(1R*,2S*)]]-3-[7-[(2-Phenylcyclopropyl) amino]-5-(butylthio)-3H-1,2,3-triazolo[4,5-d]pyrimidin-3-yl]cyclopentane-1,2-diol;
[1R-[1α,2α,3β(1R*,2S*)]]-3-[7-[(2-Phenylcyclopropyl) amino]-5-(3,3,3-trifluoropropylthio)-3H-1,2,3-triazolo[4,5-d]pyrimidin-3-yl]cyclopentane-1,2-diol;
[1R-[1α,2α,3β(1R*,2S*)]]-3-[7-[[2-(4-Chlorophenyl)cyclopropyl]amino]-5-(butylthio)-3H-1,2,3-triazolo[4,5-d]pyrimidin-3-yl]cyclopentane-1,2-diol;
[1R-[1α,2α,3β(1R,2S*)]]-3-[7[[2-(4-Fluorophenyl)cyclopropyl]amino]-5-(butylthio)-3H-1,2,3-triazolo[4,5-d]pyrimidin-3-yl]cyclopentane-1,2-diol;
[1R-[1α,2β(1R*,2S*)]]-2-[7[(2-Phenylcyclopropyl) amino]-5-(propylthio)-3H-[1,2,3]triazolo[4,5-d]pyrimidin-3-yl]cyclopentanol;
[1R-[1α,2β(1R*,2S*)]]-2-[[7-[2-(4-Methoxyphenyl)cyclopropyl]amino]-5-(propylthio)-3H-[1,2,3]triazolo[4,5-d]pyrimidin-3-yl]cyclopentanol;
[1R-[1α,2β(1R*,2S*)]]-2-[7-[[2-(3,4-Difluorophenyl)cyclopropyl]amino]-5-(propylthio)-3H-[1,2,3]triazolo[4,5-d]pyrimidin-3-yl]cyclopentanol;

or a pharmaceutically acceptable salt thereof.

14. A pharmaceutical composition comprising a compound according to claim 1 in combination with a pharmaceutically acceptable diluent, adjuvent or carrier.

15. A method of treatment of unstable or stable angina, comprising administering a therapeutically effective amount of a pharmaceutical composition comprising a compound according to claim 1 to a person in need of treatment for such a condition.

16. A method of treatment of unstable or stable angina which comprises administering a therapeutically effective amount of a compound according to claim 1 to a person in need of treatment for such a condition.

* * * * *